(12) United States Patent
Frommer et al.

(10) Patent No.: US 7,579,149 B2
(45) Date of Patent: Aug. 25, 2009

(54) METHOD AND APPARATUS TO SEPARATE MOLECULES ACCORDING TO THEIR MOBILITIES

(75) Inventors: Jane E. Frommer, San Jose, CA (US); Kerem Unal, San Jose, CA (US); Hemantha K. Wickramasinghe, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 488 days.

(21) Appl. No.: 11/047,250

(22) Filed: Jan. 31, 2005

(65) Prior Publication Data

US 2006/0172283 A1 Aug. 3, 2006

(51) Int. Cl.
*C12Q 1/68* (2006.01)
*C12P 19/34* (2006.01)
*C12M 23/00* (2006.01)
*B01D 57/02* (2006.01)

(52) U.S. Cl. ................. 435/6; 435/91.1; 435/283.1; 204/450

(58) Field of Classification Search .............. 435/6, 435/91.1, 283.1; 204/450
See application file for complete search history.

(56) References Cited

U.S. PATENT DOCUMENTS

| | | | | |
|---|---|---|---|---|
| 4,206,160 A * | 6/1980 | Suddendorf et al. | ......... | 261/78.2 |
| 4,539,089 A | 9/1985 | Binnig et al. | | |
| 5,144,148 A | 9/1992 | Eigler | | |
| 5,689,494 A * | 11/1997 | Ichikawa et al. | ............ | 369/126 |
| 5,869,829 A * | 2/1999 | Dresch | ........................ | 250/287 |
| 5,980,713 A * | 11/1999 | Davidson et al. | ............ | 204/456 |
| 6,051,189 A * | 4/2000 | Wick et al. | ............... | 422/82.01 |
| 6,350,609 B1 * | 2/2002 | Morozov et al. | ......... | 435/283.1 |
| 6,716,994 B1 * | 4/2004 | Menchen et al. | ............ | 548/455 |
| 2002/0122873 A1 * | 9/2002 | Mirkin et al. | ................ | 427/2.1 |
| 2002/0125192 A1 * | 9/2002 | Lopez et al. | ................ | 210/656 |
| 2003/0157254 A1 | 8/2003 | Mirkin et al. | | |
| 2003/0190647 A1 * | 10/2003 | Odera | ......................... | 435/6 |
| 2004/0037959 A1 | 2/2004 | Mirkin et al. | | |
| 2004/0214177 A1 | 10/2004 | Bension | | |

OTHER PUBLICATIONS

Gardiner et al, Somatic Cell Mol. Genet., vol. 12, pp. 185-195 (1986).*
Descruisseaux et al. "Electrophoresis of Composite Molecular Objects. 2. Competition Between Sieving and Frictional Effects in Polymer Solutions", Macromolecules 2001. vol. 34, pp. 5280-5286.
Mayer et al. "Theory of DNA Sequencing Using Free-Solution Electrophoresis of Protein-DNA Complexes", Analytical Chemistry, vol. 66, No. 10, May 15, 1994, pp. 1777-1780.

* cited by examiner

*Primary Examiner*—Ram R. Shukla
*Assistant Examiner*—Robert T. Crow
(74) *Attorney, Agent, or Firm*—Gibb I.P. Law Firm, LLC (57) ABSTRACT

A method and apparatus for separating molecules comprises placing different kinds of molecular species onto a probe; and introducing an electric field between the probe and a surface in proximity with the probe so that the different kinds of molecular species may be separated, wherein the different kinds of molecular species have differing mobilities, and wherein the different kinds of molecular species may be separated according to their differing mobilities, such that molecular species that have different mobilities migrate along the probe at different speeds towards the surface. The molecular species may comprise molecules. Alternatively, the molecular species may comprise molecular assemblies, wherein the molecular assemblies may comprise at least one of cells, bacteria, and viruses.

40 Claims, 7 Drawing Sheets

| Providing a probe onto which are placed different kinds of molecular species. | ~301 |

↓

| Moving at least one of the probe and a surface with respect to each other to deposit the different kinds of molecular species at different locations on the surface so that different locations are associated with different kinds of molecular species. | ~303 |

FIG. 4D

| Providing a probe onto which are placed at least one group of molecular species. | ~401 |

↓

| Positioning the probe at a location on a surface to deposit the group of molecular species at that location, wherein an electric field is applied to the probe to move the group of molecular species along the probe and onto the surface. | ~403 |

METHOD AND APPARATUS TO SEPARATE MOLECULES ACCORDING TO THEIR MOBILITIES

BACKGROUND OF THE INVENTION

1. Field of the Invention

The embodiments of the invention generally relate to molecular separation methods, and more particularly to macromolecular separation based on differential mobility.

2. Description of the Related Art

In biology and chemistry, there is wide interest in the ability to sort polyelectrolytes and molecules by their length, in particular for deoxyribonucleic acid (DNA) sequencing purposes. The need for genome sequencing and the demand for genetic diagnosis and testing tools for health related applications require high throughput and low cost sequencing methods. Electrophoresis is generally described as the movement of charged molecules, such as proteins in the presence of an electric field. Generally, the separation of molecules in an electric field is based on the size, shape, and charge of a particular molecule. A description of end label free-solution electrophoresis (ELFSE) is provided in Mayer et al., "Theory of DNA Sequencing Using Free-Solution Electrophoresis of Protein-DNA Complexes," Anal. Chem. 1994, 66, 1777-1780, the complete disclosure of which in its entirety is herein incorporated by reference.

Other conventional electrophoresis techniques generally consist of slab or capillary electrophoresis using dilute or entangled polymers. Although those techniques have been shown to successfully separate fragments with hundreds of bases (i.e., DNA bases—adenine, thymine, guanine, and cytosine) the time required to achieve an efficient separation is a major limitation to the development of high throughput sequencing systems. To increase the mobility of polyelectrolytes in sieving matrixes and, hence, in DNA sequencing speed, higher electric fields are often used. However, these resulting higher velocities and higher electric fields generally lead to a decrease in resolution and a degradation of the sieving medium. Therefore, new physical separation mechanisms are necessary in order to improve throughput by both decreasing the size of the sampled population and increasing the processing speed.

SUMMARY OF THE INVENTION

In view of the foregoing, an embodiment of the invention provides a method comprising placing different kinds of molecular species onto a probe; and introducing an electric field between the probe and a surface in proximity with the probe so that the different kinds of molecular species may be separated, wherein the different kinds of molecular species have differing mobilities, and wherein the different kinds of molecular species may be separated according to their differing mobilities, such that molecular species that have different mobilities migrate along the probe at different speeds towards the surface. The molecular species may comprise molecules. Alternatively, the molecular species may comprise molecular assemblies, wherein the molecular assemblies may comprise at least one of cells, bacteria, and viruses.

Preferably, the method further comprises introducing an electric field by applying a potential between the probe and the surface. Preferably, the method further comprises introducing an electric field as a series of pulses between the surface and an upper portion of the probe such that groups of molecular species with differing mobilities may be separated from the probe according to at least one of pulse height and width. Preferably, the method further comprises introducing an electric field to the probe to position the molecular species away from a bottom portion of the probe prior to the molecular species migrating towards the surface. Preferably, the method further comprises introducing an electric field on the probe to position the molecular species towards a physical barrier on the probe away from a bottom portion of the probe prior to the molecular species migrating towards the surface.

The different kinds of molecular species may be separated at respective locations substantially centered about respective points separated by at least a radius of the probe. Also, label molecular species may be attached to at least some of the molecular species to change the mobility of the at least some molecular species. Moreover, the molecular species may comprise different single-stranded DNA fragments that are separated on the surface into respective groups of DNA fragments having similar molecular weights. Furthermore, the molecular species may comprise different DNA base pairs. Additionally, the molecular species may comprise different fluorescently tagged DNA fragments that are separated on the surface into respective groups of DNA fragments having similar molecular weights, wherein the fluorescent tags may be detected to decipher a DNA sequence. Preferably, the method further comprises exposing the probe to at least one chemical species such that a coefficient of friction of the probe is altered, thereby promoting enhanced separation of the molecular species, wherein the at least one chemical species may comprise chemical coatings on the probe.

Another aspect of the invention provides a method comprising placing groups of different kinds of molecular species onto a probe tip; positioning the probe tip over a surface; and introducing an electric field to the probe tip to cause at least one of: releasing of the groups of molecular species at specified locations on the surface and releasing of the groups of molecular species at specific times, wherein each specified location corresponds to a particular group of molecular species. The groups of molecular species may be tagged, wherein the groups of tagged molecular species on the surface may be identified by at least one of atomic force microscopy, electromagnetic absorption, electromagnetic resonance, and fluorescence. Moreover, the groups of tagged molecular species released from the probe tip may be detected as a time sequence. The groups of tagged molecular species may be identified by any of scanning tunneling microscope current, electromagnetic absorption, electromagnetic resonance, and fluorescence.

Furthermore, molecular species that have different mobilities migrate along the probe tip at different speeds towards the surface. Preferably, the method further comprises positioning the molecular species away from a bottom portion of the probe tip prior to the molecular species migrating towards the surface. Preferably, the electric field is applied between the surface and an upper portion of the probe tip. The label molecular species may be attached to at least some of the molecular species to change at least one of charge, mass, and frictional coefficient of the at least some molecular species. Additionally, any of different DNA base pairs and single strand fragments may be deposited at least one of different specified locations and different times. Preferably, the method further comprises exposing the probe tip to at least one chemical species such that a coefficient of friction of the probe tip is altered, thereby promoting enhanced separation of the molecular species.

Another embodiment of the invention provides an apparatus comprising a probe tip carrying different kinds of molecular species; a surface proximate to the probe tip; and means for causing the different kinds of molecular species to be released at different locations on the surface so that different locations are associated with different kinds of molecular species. Preferably, the means comprises a voltage source adapted to introduce an electric field to the probe tip such that molecular species that have different mobilities migrate along the probe tip at different speeds towards the surface. Preferably, the apparatus further comprises means for positioning the molecular species away from a bottom portion of the probe tip prior to the molecular species migrating towards the surface. Additionally, the different kinds of molecular species may be separated at respective locations substantially centered about respective points separated by at least a radius of the probe tip. Preferably, the apparatus further comprises means for identifying groups of molecular species deposited on the surface. Preferably, the apparatus further comprises means for identifying groups of molecular species released from the probe tip in a time sequence.

Another aspect of the invention provides a method comprising providing a probe onto which are placed different kinds of molecular species; and moving at least one of the probe and a surface with respect to each other to deposit the different kinds of molecular species at different locations on the surface so that different locations are associated with different kinds of molecular species. Preferably, the method further comprises applying an electric field to the probe so that different kinds of molecular species move along the probe at different speeds towards the surface. The different kinds of molecular species may have different charge-to-mass ratios. Preferably, the method further comprises applying an electric field to the probe to position the different kinds of molecular species away from the bottom of the probe, prior to moving the molecular species towards the surface for the purpose of separating them. The electric field may be applied between the surface and the top of the probe.

Moreover, the different locations may be separated by at least 10 nanometers. Alternatively, the different locations may be separated by at most 1 meter. Still alternatively, the different locations may be separated by at most 1 centimeter. Furthermore, the label molecular species may be attached to at least some of the molecular species to change at least one of charge and mass of the at least some molecular species. The method may be applied to separate different DNA fragments into respective groups on the surface. Also, different DNA base pairs may be deposited at different locations. The probe may be exposed to a solution so that the friction of coefficient of the probe is altered, thereby promoting improved separation of the different kinds of molecular species.

Another aspect of the invention provides a method comprising providing a probe onto which are placed at least one group of molecular species; and positioning the probe at a location on a surface to deposit the group of molecular species at that location, wherein an electric field is applied to the probe to move the group of molecular species along the probe and onto the surface.

The embodiments of the invention increase the speed of separation of molecules according to their molecular weight or chemical composition by three to four orders of magnitude as compared to the example of conventional electrophoresis techniques. The embodiments of the invention provide a technique that scales the separation process down to a nanometer length scale to hasten the separation speed. A physical separation mechanism for molecules or molecular assemblies under a field can also be achieved by incorporating labels to the molecules to be separated therefore changing their friction coefficient and mobilities.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which.

DETAILED DESCRIPTION OF PREFERRED EMBODIMENTS OF THE INVENTION

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for new physical separation mechanisms in order to increase the throughput in the separation of mixtures. The embodiments of the invention achieve this by providing methods of separating molecules and molecular assemblies based on the control of the movement of molecules with an applied field. Referring now to the drawings and more particularly to FIGS. 1 through 4D where similar reference characters denote corresponding features consistently throughout the figures, there are shown preferred embodiments of the invention.

As used in the context of the embodiments of the invention, mobility is defined as the velocity divided by the electric field. Furthermore, the embodiments of the invention refer to molecular species, which may comprise molecules. Alternatively, the molecular species may comprise molecular assemblies, wherein the molecular assemblies may comprise at least one of cells, bacteria, and viruses. In the descriptions below, DNA is used as an example of the type of molecules used in practicing the embodiments of the invention. However, the embodiments of the invention are not limited to DNA molecules. To prepare for the separation of DNA fragments, a label (not shown) is first attached to the macromolecules. This allows for a differential response to an electric field in the separation process. Labels are typically drawn from classes of molecules that are compatible with the parent molecule, including proteins and fluorescent tags.

Equation (1) describes the proportionality relationship between the labeled molecule's mobility and the mobility of its unlabelled counterpart, taking into account the additional charge and friction introduced by the labeling.

$$\mu_{L-DNA}(M) = \mu_{DNA}(M) \frac{M + \beta}{M + \alpha} \qquad (1)$$

where $\mu_{L-DNA}$ is the mobility of the labeled DNA fragment; M is the number of bases; $\mu_{DNA}$ is the mobility of the unlabeled DNA fragment; $\alpha$ is the ratio between the frictional coefficient of the labeled end relative to the frictional coefficient of a single DNA base unit; and $\beta$ is the ratio of the electric charge of the label relative to the electric charge of a single DNA base unit. Thus, $\alpha$ and $\beta$ are dimensionless quantities. It can be seen from equation (1) that in order for molecules to be sorted on the basis of their sizes, $\alpha \neq \beta$.

Figure 1:
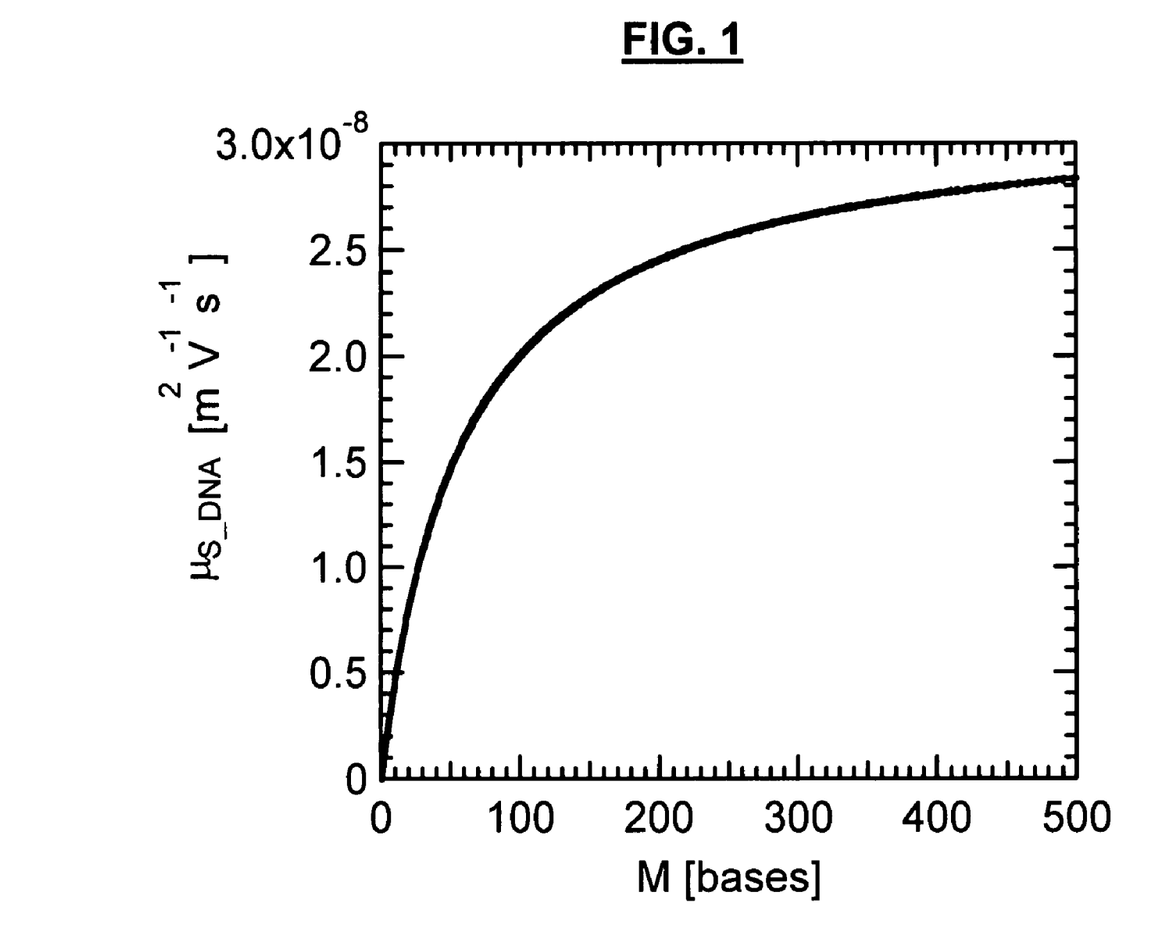
FIG. 1 is a graphical representation illustrating the mobility ($\mu_{S\text{-}DNA}$) of streptavidin labeled DNA fragments as a function of the number of bases (M)

An example of a series of DNA strands labeled with streptavidin is given in FIG. 1. The graph illustrates the relationship of sorting molecules by their number of bases; i.e., on the basis of the mobility of their fragment size. The graph provided in FIG. 1 is constructed from values of $\alpha$ and $\beta$ culled from Desruisseaux, C. et al., "Electrophoresis of Composite Molecular Objects," Macromolecules 2001, 34, 5280-5286, the complete disclosure of which, in its entirety, is herein incorporated by reference. FIG. 1 generally indicates that there is a positive asymptotic relationship between the number of DNA bases and the mobility of the molecules; that is, the greater the number of bases, the higher the mobility.

Figure 2A:
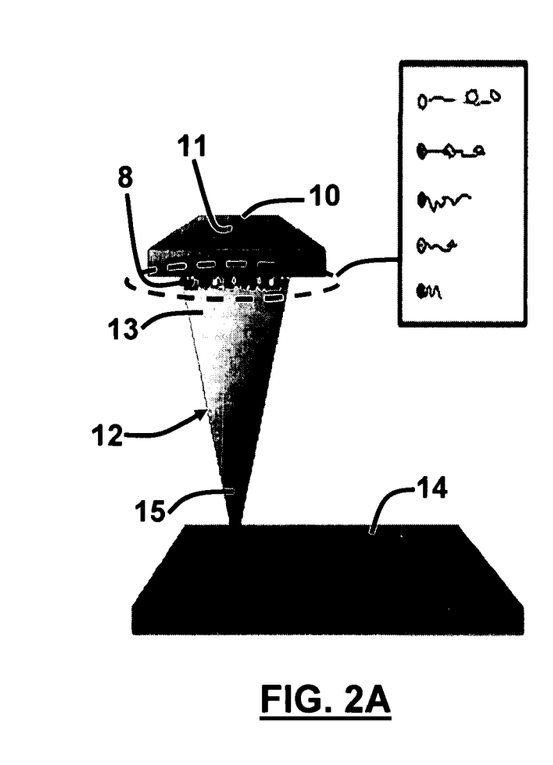
FIG. 2A illustrates an apparatus used for implementing a methodology according to an embodiment of the invention.
Figure 2B:
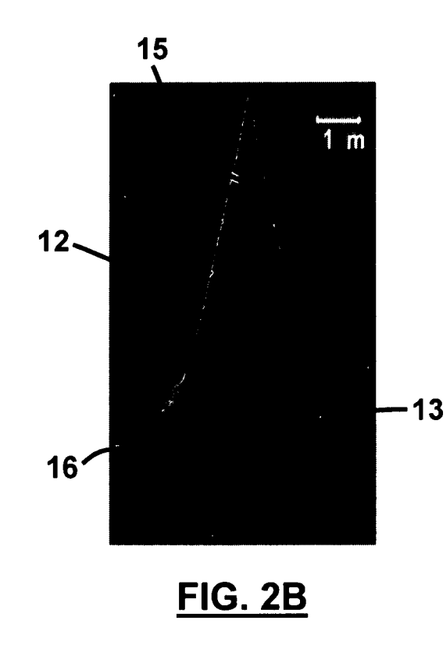
FIG. 2B is a scanning electron microscope (SEM) image of a configuration of an atomic force microscope (AFM) tip experimentally created for an embodiment of the invention.
Figure 2C:
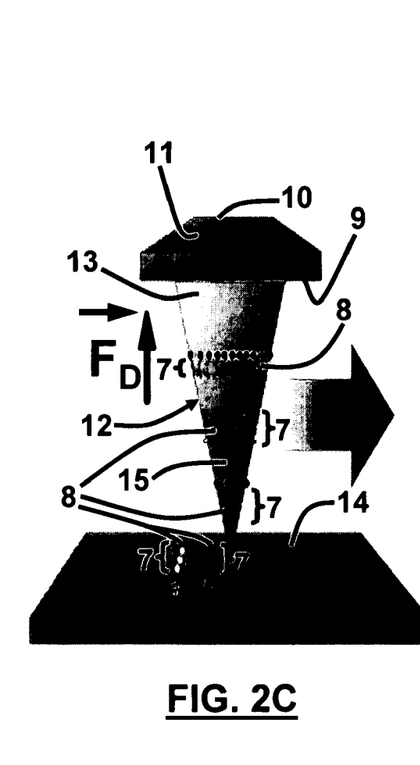
FIG. 2C illustrates the apparatus of FIG. 2A during operation according to an embodiment of the invention.

In this example, the embodiments of the invention use a scanning probe microscope (SPM) tip to separate DNA fragments from one another. FIGS. 2A through 2C illustrate the apparatus used to separate DNA fragments according to an embodiment of the invention. The scanning probe equipment used in this example is representative of the instrumentation of the atomic force microscopy (AFM) community.

As shown in FIG. 2A, a cantilever structure 10 is attached to an AFM tip 12. The top side 11 of the cantilever structure 10 is metal-coated in order to serve as a top electrode. The tip 12 is preferably covered with a chemical coating to make it chemically compatible with the fragments to be separated. One example of such a coating for the tip 12 is polyethylene glycol (PEG). The mixture of molecular fragments 8 to be separated is shown in FIG. 2A as a band (within the dotted encircled portion of FIG. 2A) at the upper portion 13 of the tip 12 before the application of a voltage (or bias) causing an electric field, $F_D$. The flat substrate plane 14 shown beneath the tip 12 serves as the second electrode. The substrate 14 can also be derivatized chemically to be compatible with the DNA strands. One example of such a coating for the substrate 14 is amino-propyl-triethoxy-silane (APTES).

The length and shape of the tip 12 are generally in the range of dimensions given for typical atomic force microscope cantilever-tip assemblies: 1-10 μm long, terminating in a radius of curvature of 1-10 nm. The material of the tip 12, cantilever 10, and substrate 14 in one embodiment of the invention is silicon, although other suitable materials could be used.

FIG. 2B illustrates an SEM image of an inverted configuration of the AFM tip 12, which was experimentally created. FIG. 2B shows the addition of a trench-like repository 16 at the broad base portion of the tip 12, which is actually the upper portion 13 of the tip 12, for confining the molecular mixture prior to application of the electric field, $F_D$. The trench 16 acts as a physical barrier to define the starting point previous to migration of the molecular species 8. In other words, prior to separating the mixture of molecular species 8, one can confine them to the upper portion 13 of the tip 12. This can be performed physically or topographically using the trench 16 as a physical barrier. This can also be performed by introducing a field of opposite polarity that will later be used to separate the molecular species 8. This opposite polarity will force the molecular mixture 8 to the starting point of its migration pathway: the upper portion 13 of the tip 12. The molecular mixture 8 is applied as a solution in appropriate solvent. In one embodiment, the molecular species 8 are applied in an aqueous solution to the tip 12 operated under ambient conditions by dipping the tip into a droplet of the solution.

FIG. 2C illustrates the apparatus shown in FIG. 2A during operation. In particular, a voltage is applied causing an electric field, $F_D$, to be introduced between the conductive coating on the backside 9 of the cantilever 10 and the conducting substrate 14. The strength of the electric field, $F_D$, depends on many factors, including the dimensions of the cantilever 10, tip 12, and substrate 14 and the nature of the molecular species 8 to be separated. In this particular example of the separation shown in FIG. 3A, the range of the strength of the electric field, $F_D$, is $10^5$-$10^6$ volts/meter.

Prior to application of the electric field, $F_D$, used for separating the molecular species 8, the polarity of the molecular species 8 confines the molecular species 8 to the top 13 of the tip 12, as shown in FIG. 2A. This confinement may be aided by the application of a small field of opposite polarity. In this example, negatively charged DNA fragments 8 are initially attracted to the top 13 of the AFM tip 12, and act as a starting point for the sequencing procedure. Upon application of an electrical bias (not shown) from an electrical source (not shown) between the tip 12 and the substrate 14, the electric field, $F_D$, drives the molecular species 8 to the opposite end 15 of the tip 12 while the tip 12 scans relative to the surface of the substrate 14. Because the velocity of the different molecular fragments 8 is a function of size, molecular species 8 travel down the tip 12 in groups 7 with the same (i.e., similar) mass. These groups 7 of molecular species 8 are then deposited on the surface of the substrate 14, whereby each group 7 of molecular species 8 is deposited in a specific location a, b on the scanned surface 14. By measuring the position of the molecular species 8 on the surface 14 relative to one another, one can then determine the relative number of bases of the different molecular fragments 8 accordingly.

The arrow pointing to the right in FIG. 2C denotes the direction of movement of the tip 12 and cantilever 10 relative to the substrate 14. The difference in deposition times ($\Delta t$) for two groups of molecular species 8 of similar mobilities is:

$$\Delta t = d\Delta v/v^2 \qquad (2)$$

where d is the length of tip, v is the velocity of individual species, and $\Delta v$ is the differential velocity between the two groups 7 of molecular species 8. The spacing between those two groups on a scanned substrate ($\Delta x$) is:

$$\Delta x = V\Delta t \qquad (3)$$

where V is the velocity of the scanned substrate ($\Delta x$), and $\Delta t$ is the time interval between the deposition of the two groups 7 of molecular species 8.

The resolution achieved using the apparatus and method provided in FIGS. 2A through 2C was 10 nm, based on a 10 nm feature size detected for each group 7 of molecular species 8 by the particular detecting probe used in the experiment. This scale is not an intrinsic limitation, as resolution is affected by detection sensitivity, probe dimensions and field intensity, among many other factors.

Figure 3A:
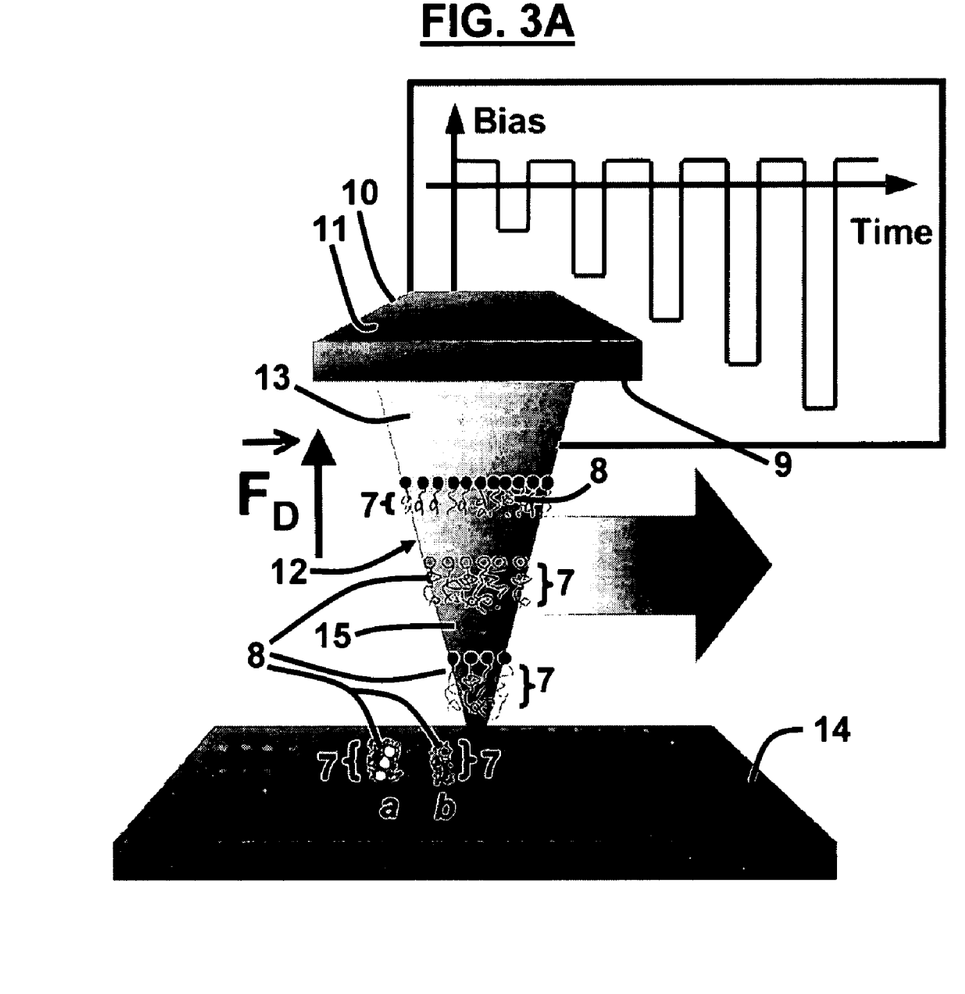
FIG. 3A illustrates the apparatus of FIG. 2C during operation according to an embodiment of the invention that involves introducing the electric field according to an algorithm of pulse height (voltage)

FIG. 3A illustrates the apparatus shown in FIG. 2A during operation. In particular, an electric field, $F_D$, is introduced between the conductive coating on the backside 9 of the cantilever 10 and the conducting surface of the substrate 14. The electric field, $F_D$, is applied in a pulsed manner so that the deposition of molecular species 8 with defined molecular weights is chosen by the pulse height or pulse width.

Detection of deposited molecular species 8 on the surface 14 can take place with a number of detection schemes including optics, profilometry, or electrical characterization, nonexclusively. The detection scheme used in the experiments conducted in accordance with the embodiments of the invention was the well-known lateral force mode of the AFM.

According to the embodiments of the invention, there is no obvious limit on the number of molecular species 8 that can be separated in the manner provided by the embodiments of the invention, given the appropriate adjustment of reaction parameters (e.g., voltage, pulsing protocols, etc.) and the capability of scaling up into arrays of probes.

Figure 3B:
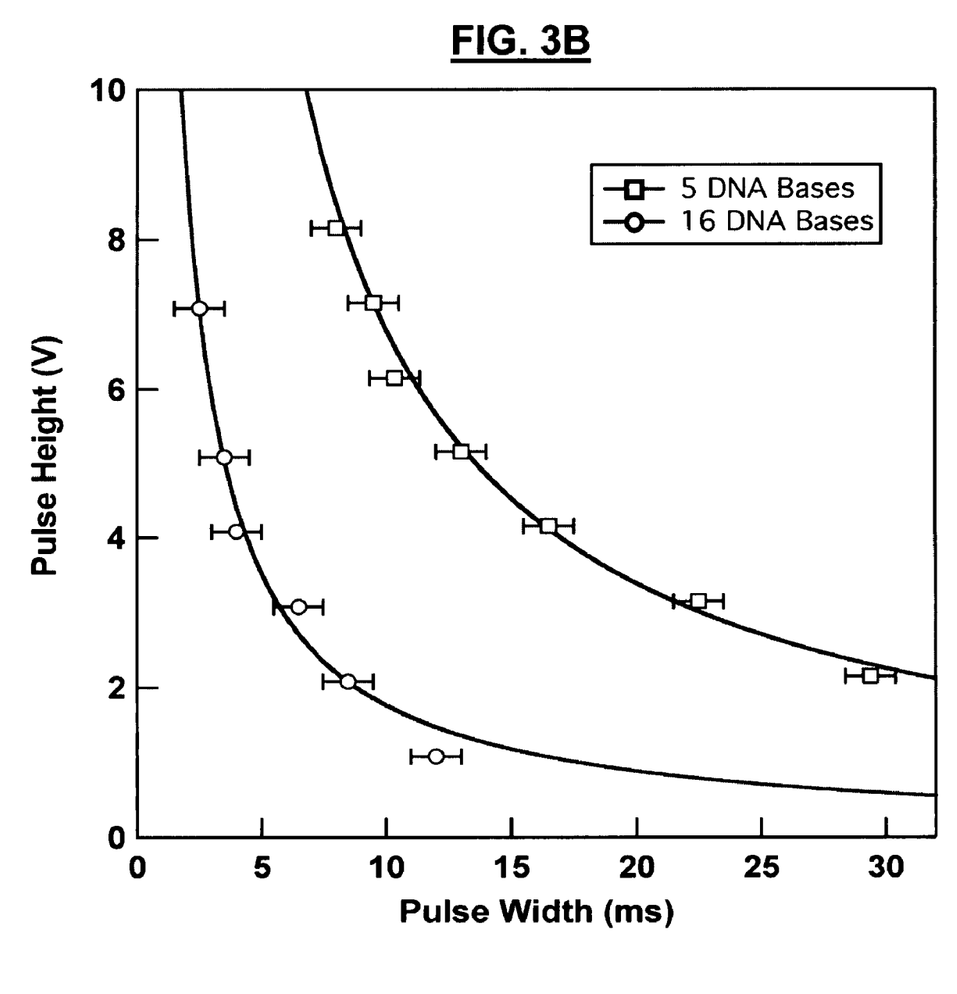
FIG. 3B is a graphical representation illustrating the threshold pulse height as a function of the pulse width for 5- and 16-base long single stranded DNA fragments.

Experimental results: The mobility of two different DNA fragments was measured by detecting the threshold electrical bias required to transfer molecular species 8 to the surface 14. The electrical bias was applied in pulses characterized by pulse width (time) and pulse height (voltage) as shown in FIG. 3B. A mobility of $\mu_5 = 1.96 \cdot 10^{-5}$ (cm$^2$/Vs) and $\mu_{16} = 7.13 \cdot 10^{-5}$ (cm$^2$/Vs) was obtained for single stranded DNA fragments of 5 and 16 bases, respectively. What is remarkable about these results is that mobilities obtained on the representative molecular species 8 are numerically consistent with literature values, but were obtained from an unprecedented small population size (0.1 zeptomoles, $10^{-21}$ moles, <100 molecules). Conventional measurements of molecular mobilities are collected on populations approximately ten orders of magnitude larger. Additionally, the measurements attained according to the embodiments of the invention are performed on a time scale three to four orders of magnitude faster than conventional methods.

The observed difference in mobility allows the separation of the two populations (5 and 16 bases) with the methods provided by the presented embodiment of the invention. A sensitivity of 5-10 molecules or 0.1 zeptomole is deduced from the observed 10 nm size of molecular species groups 7 detected on the surface 14.

Figure 3C:
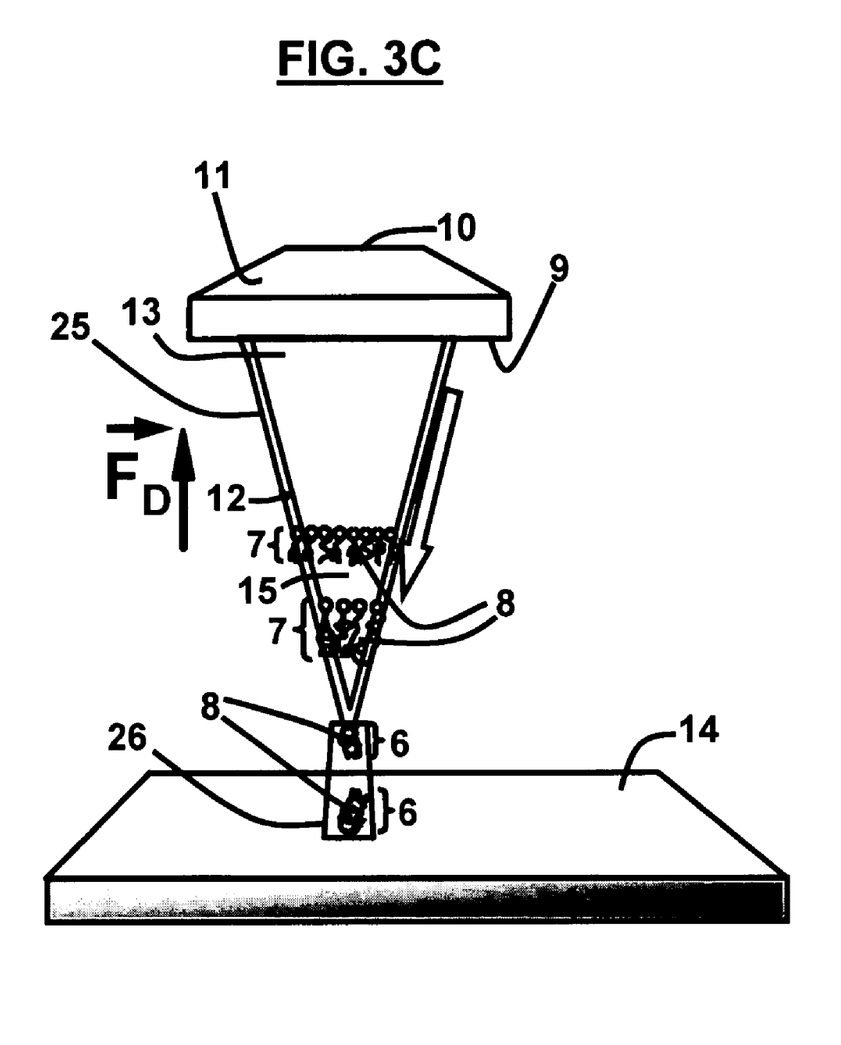
FIG. 3C illustrates the apparatus of FIG. 2C during operation according to an embodiment of the invention that involves introducing the electric field and detecting the separation of molecules or molecular assemblies according to time as they pass from tip to substrate.

Another aspect of the invention is illustrated in FIG. 3C which illustrates a method of separating molecular species 8, wherein the method comprises attaching molecular species 8 comprising differing molecular weights or chemical natures to a probe tip 12 and monitoring the vertical stream (denoted by the downward sloping arrow in FIG. 3C) of separated components 6 leaving the probe tip 12 for the separation of molecular species 8 or molecular assemblies based on differential mobilities. This detection scheme does not require the scanning motion of the underlying substrate 14; instead of employing a scanned substrate 14 to capture the separated molecular species 8, the streaming exit flow is monitored by a detection method. This detection method, which utilizes a detector 26, can be optical, electrical, magnetic, nonexclusively. This method further comprises exposing the scanning probe tip 12 to a coating or a solution 25 such that a coefficient of friction of the scanning probe tip 12 is altered, thereby promoting enhanced separation of the molecular species 8 according to their molecular weights.

Figure 4A:
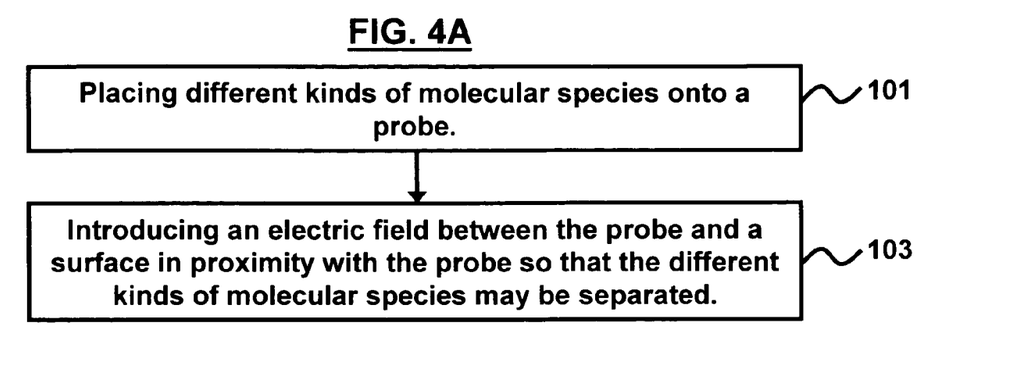
FIGS. 4A through 4D are flow diagrams illustrating preferred methods according to the embodiments of the invention.

Another aspect of the invention is illustrated in the flowcharts of FIGS. 4A through 4D, which includes descriptions which refer to components provided in FIGS. 1 though 3. FIG. 4A illustrates a method comprising placing (101) different kinds of molecular species 8 onto a probe 12; and introducing (103) an electric field, $F_D$, between the probe 12 and a surface 14 in proximity with the probe 12 so that the different kinds of molecular species 8 may be separated, wherein the different kinds of molecular species 8 have differing mobilities, and wherein the different kinds of molecular species 8 may be separated according to their differing mobilities, such that molecular species that have different mobilities migrate along the probe 12 at different speeds towards the surface 14.

The molecular species 8 may comprise molecules. Alternatively, the molecular species 8 may comprise molecular assemblies, wherein the molecular assemblies may comprise at least one of cells, bacteria, and viruses. Preferably, the method further comprises introducing an electric field, $F_D$, by applying a potential between the probe 12 and the surface 14. Alternatively, the method further comprises introducing an electric field, $F_D$, as a series of pulses between the surface 14 and an upper portion 13 of the probe 12 such that groups 7 of molecular species 8 with differing mobilities may be separated from the probe 12 according to at least one of pulse height and width.

Alternatively, the method further comprises introducing an electric field, $F_D$, to the probe 12 to position the molecular species 8 away from a bottom portion 15 of the probe 12 prior to the molecular species 8 migrating towards the surface 14. Still alternatively, the method further comprises introducing an electric field, $F_D$, on the probe 12 to position the molecular species 8 towards a physical barrier 16 on the probe 12 away from a bottom portion 15 of the probe 12 prior to the molecular species 8 migrating towards the surface 14. The different kinds of molecular species 8 may be separated at respective locations a, b substantially centered about respective points separated by at least a radius of the probe 12. Also, label molecular species (not shown) may be attached to at least some of the molecular species 8 to change the mobility of the at least some molecular species 8. Moreover, the molecular species 8 may comprise different single-stranded DNA fragments that are separated on the surface into respective groups of DNA fragments having similar molecular weights. Furthermore, the molecular species 8 may comprise different DNA base pairs.

Additionally, the molecular species 8 may comprise different fluorescently tagged DNA fragments that are separated on the surface 14 into respective groups of DNA fragments having similar molecular weights, wherein the fluorescent tags may be detected to decipher a DNA sequence. Preferably, the method further comprises exposing the probe 12 to at least one chemical species such that a coefficient of friction of the probe 12 is altered, thereby promoting enhanced separation of the molecular species 8, wherein the at least one chemical species may comprise chemical coatings 25 on the probe 12.

Figure 4B:
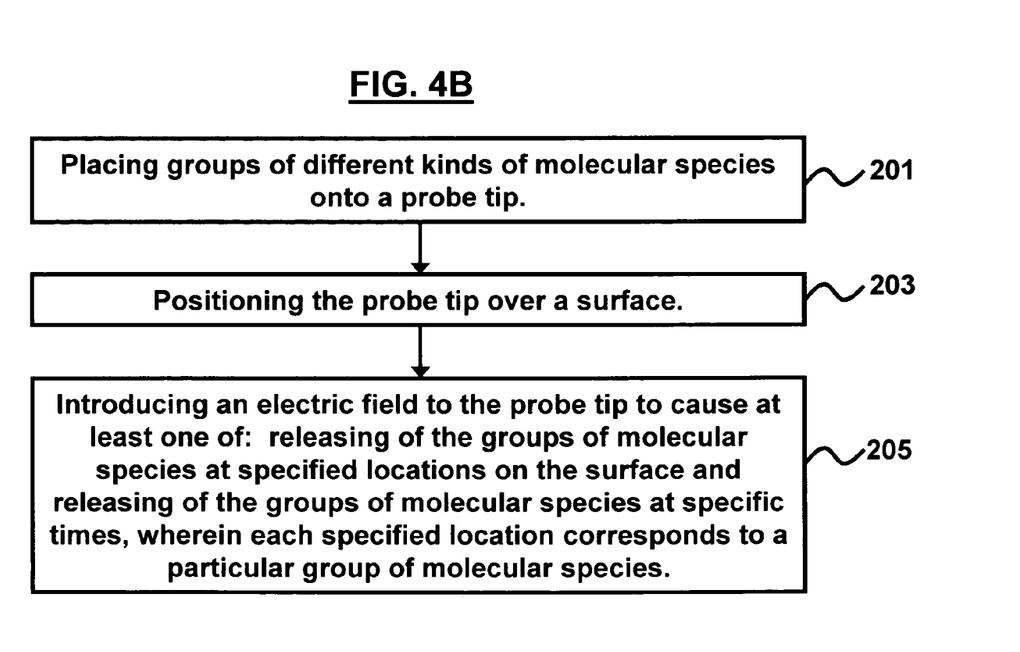

FIG. 4B illustrates a method comprising placing (201) groups 7 of different kinds of molecular species 8 onto a probe tip 12; positioning (203) the probe tip 12 over a surface 14; and introducing (205) an electric field, $F_D$, to the probe tip 12 to cause at least one of: releasing of the groups 7 of molecular species 8 at specified locations a, b on the surface 14 and releasing of the groups 7 of molecular species 8 at specific times, wherein each specified location a or b corresponds to a particular group of molecular species 8. The groups 7 of molecular species 8 may be tagged, wherein the groups 7 of tagged molecular species 8 on the surface 14 may be identified by at least one of atomic force microscopy, electromagnetic absorption, electromagnetic resonance, and fluorescence.

Moreover, the groups 7 of tagged molecular species 8 released from the probe tip 12 may be detected as a time sequence. The groups 7 of tagged molecular species 8 may be identified by any of scanning tunneling microscope current, electromagnetic absorption, electromagnetic resonance, and fluorescence. Furthermore, molecular species 8 that have different mobilities migrate along the probe tip 12 at different speeds towards the surface 14. Preferably, the method further comprises positioning the molecular species 8 away from a bottom portion of the probe tip 12 prior to the molecular species 8 migrating towards the surface 14. Preferably, the electric field, $F_D$, is applied between the surface 14 and an upper portion of the probe tip 12. The label molecular species may be attached to at least some of the molecular species 8 to change at least one of charge, mass, and frictional coefficient of the at least some molecular species 8.

Additionally, any of different DNA base pairs and single strand fragments may be deposited at least one of different specified locations a, b and different times. Preferably, the method further comprises exposing the probe tip 12 to at least one chemical species such that a coefficient of friction of the probe tip 12 is altered, thereby promoting enhanced separation of the molecular species 8.

Figure 4C:
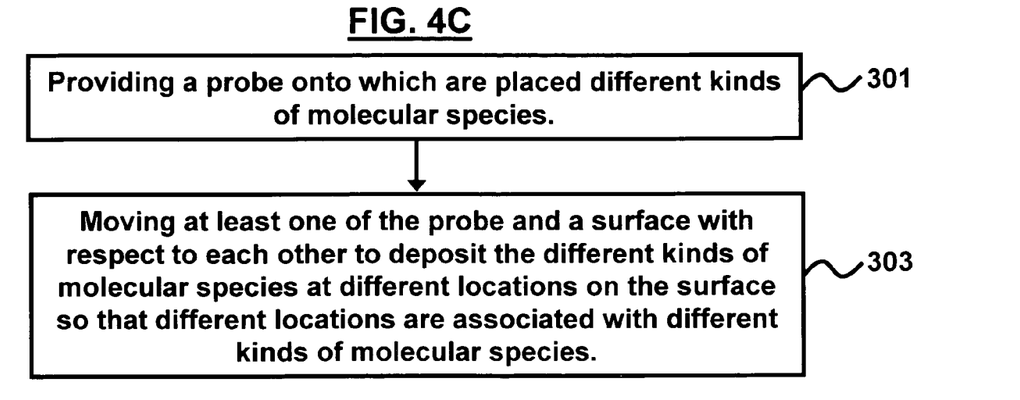

FIG. 4C illustrates a method comprising providing (301) a probe 12 onto which are placed different kinds of molecular species 8; and moving (303) at least one of the probe 12 and a surface 14 with respect to each other to deposit the different kinds of molecular species 8 at different locations a, b on the surface 14 so that different locations a, b are associated with different kinds of molecular species 8. Preferably, the method further comprises applying an electric field, $F_D$, to the probe 12 so that different kinds of molecular species 8 move along the probe 12 at different speeds towards the surface 14. The different kinds of molecular species 8 may have different charge-to-mass ratios.

Preferably, the method further comprises applying an electric field, $F_D$, to the probe 12 to position the different kinds of molecular species 8 away from the bottom 15 of the probe 12, prior to moving the molecular species 8 towards the surface 14 for the purpose of separating them. The electric field, $F_D$, may be applied between the surface 14 and the top 13 of the probe 12. Moreover, the different locations a, b may be separated by at least 10 nanometers. Alternatively, the different locations a, b may be separated by at most 1 meter. Still alternatively, the different locations a, b may be separated by at most 1 centimeter. Furthermore, the label molecular species may be attached to at least some of the molecular species 8 to change at least one of charge and mass of the at least some molecular species 8. The method may be applied to separate different DNA fragments into respective groups 7 on the surface 14. Also, different DNA base pairs may be deposited at different locations a, b. The probe 12 may be exposed to a solution so that the friction of coefficient of the probe 12 is altered, thereby promoting improved separation of the different kinds of molecular species 8.

Figure 4D:
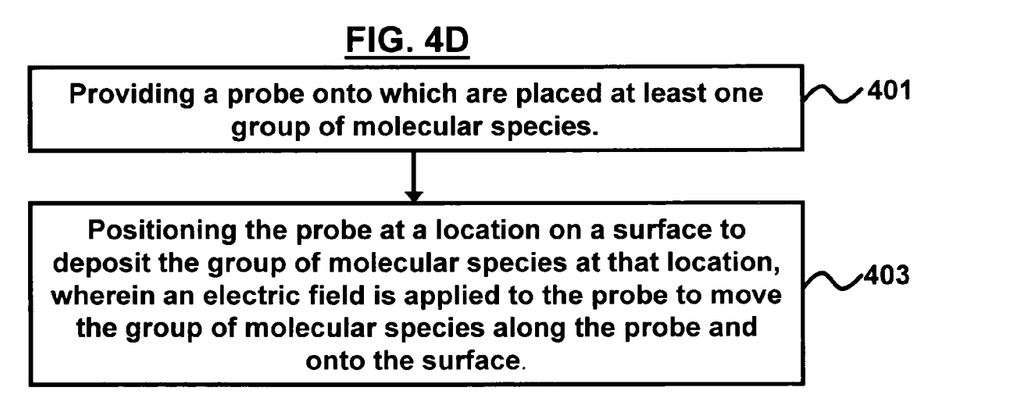

FIG. 4D illustrates a method comprising providing (401) a probe 12 onto which are placed at least one group of molecular species 8; and positioning (403) the probe 12 at a location a, b on a surface 14 to deposit the group 7 of molecular species 8 at that location a, b, wherein an electric field, $F_D$, is applied to the probe 12 to move the group 7 of molecular species 8 along the probe 12 and onto the surface 14.

The embodiments of the invention increase the speed of separation of molecular species 8 according to their molecular weight by three to four orders of magnitude as compared to convention in the example of electrophoresis techniques. The embodiments of the invention provide a technique that scales the electrophoresis process down to a nanometer length scale that hastens the sequencing speed. The embodiments of the invention provide a technique that narrows the electrophoresis process down to a spatially and temporally localized event.

The above description of the probe apparatus is not limited to tip (traditional conical) geometries; it may also include fibers, wires, dots, nonexclusively. Moreover, the separation method described above is not limited to charged species; separation can also occur to non-charged molecular species 8 or their assemblies on the basis of interfacial or adhesion energies, on the basis of field or concentration gradients. Again, as used in the context of the embodiments of the invention molecules and molecular assemblies can comprise biological systems such as viruses and cells. Furthermore, molecules and molecular assemblies do not have to be biological. Additionally, the detection schemes described above are not limited to capturing the molecular species 8 on a scanned substrate 14. Rather, the stream of separated molecules 8 exiting the probe tip 12 can be analyzed real-time as a function of exit time by such means as optics, current (e.g., tunneling), magnetic or electric field, as illustrated in FIG. 3C.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. A method comprising:
    placing different kinds of molecular species onto a scanning probe microscope tip; and
    introducing a first electric field between said scanning probe microscope tip and a substrate so that said different kinds of molecular species traverse said scanning probe microscope tip to be separated.

2. The method of claim 1, wherein different kinds of molecular species have differing mobilities, and wherein said different kinds of molecular species are separated according to their differing mobilities, such that said different kinds of molecular species that have different mobilities migrate along said scanning probe microscope tip at different speeds towards said substrate.

3. The method of claim 1, further comprising introducing a second electric field of opposite polarity to that of said first electric field between said scanning probe microscope tip and said substrate, to confine said different kinds of molecular species to a broad base portion of said scanning probe microscope tip.

4. The method of claim 1, wherein said first electric field comprises a series of pulses such that groups of molecular species with differing mobilities are separated from said scanning probe microscope tip according to at least one of pulse height and width.

5. The method of claim 1, wherein said first electric field positions said different kinds of molecular species away from a base portion of said scanning probe microscope tip, prior to said different kinds of molecular species migrating towards said substrate.

6. The method of claim 1, further comprising introducing a second electric field, of opposite polarity to said first electric field, on said scanning probe microscope tip to position said molecular species towards a physical barrier of a base portion of said scanning probe microscope tip prior to said molecular species migrating towards said substrate.

7. The method of claim 1, wherein said different kinds of molecular species are separated at respective locations on said substrate substantially centered about respective points separated by at least a radius of said scanning probe microscope tip.

8. The method of claim 2, wherein labels, including at least one of proteins and fluorescent tags, are attached to at least some of said different kinds of molecular species, such that said attaching changes the mobility of said at least some of said different kinds of molecular species.

9. The method of claim 1, wherein said different kinds of molecular species comprise different single-stranded DNA fragments that are separated on said substrate into respective groups of DNA fragments having similar molecular weights.

10. The method of claim 1, wherein said different kinds of molecular species comprise different DNA base pairs.

11. The method of claim 8, wherein said different kinds of molecular species comprise different fluorescently tagged DNA fragments that are separated on said substrate into respective groups of DNA fragments having similar molecular weights.

12. The method of claim 11, wherein the fluorescent tags are detected to decipher a DNA sequence.

13. The method of claim 1, further comprising exposing said scanning probe microscope tip to at least one chemical species such that a coefficient of friction of said scanning probe microscope tip is altered, thereby promoting enhanced separation of said different kinds of molecular species.

14. The method of claim 13, wherein said at least one chemical species comprise chemical coatings on said scanning probe microscope tip.

15. The method of claim 1, wherein said different kinds of molecular species comprise molecules.

16. The method of claim 1, wherein said different kinds of molecular species comprise molecular assemblies.

17. The method of claim 16, wherein said molecular assemblies comprise at least one of cells, bacteria, and viruses.

18. A method comprising:
placing groups of different kinds of molecular species onto a scanning probe microscope tip;
positioning said scanning probe microscope tip over a substrate; and
introducing an electric field between said scanning probe microscope tip and said substrate to cause at least one of: releasing of said groups of different kinds of molecular species at specified locations on said substrate, and releasing of said groups of different kinds of molecular species at specific times on said substrate, wherein each specified location corresponds to a particular group of said groups of different kinds of molecular species.

19. The method of claim 18, wherein said groups of different kinds of molecular species are labeled by at least one of proteins and fluorescent tags.

20. The method of claim 19, wherein labeled groups on said substrate are identified by at least one of atomic force microscopy, electromagnetic absorption, electromagnetic resonance, and fluorescence.

21. The method of claim 20, wherein the labeled groups released from said scanning probe microscope tip are detected as a time sequence.

22. The method of claim 19, wherein said labeled groups are identified by any of electromagnetic absorption, electromagnetic resonance, and fluorescence.

23. The method of claim 18, wherein said groups of different kinds of molecular species that have different mobilities migrate along said scanning probe microscope tip at different speeds towards said substrate.

24. The method of claim 23, further comprising positioning said groups of different kinds of molecular species close to a base portion of said scanning probe microscope tip prior to said groups of different kinds of molecular species migrating towards said substrate.

25. The method of claim 18, wherein said electric field is applied between said substrate and a base portion of said scanning probe microscope tip.

26. The method of claim 20, wherein said labeled groups are attached to at least some of said groups of different kinds of molecular species to change at least one of charge, mass, and frictional coefficient of said at least some of said groups of different kinds of molecular species.

27. The method of claim 25, wherein any of said groups of different kinds of molecular species are deposited at least one of different specified locations and different times.

28. The method of claim 27, further comprising exposing said scanning probe microscope tip to at least one chemical species, such that a coefficient of friction of said scanning probe microscope tip is altered, thereby promoting enhanced separation of said groups of different kinds of molecular species.

29. A method comprising:
providing a scanning probe microscope tip onto which are placed different kinds of molecular species; and
moving at least one of said scanning probe microscope tip and a substrate with respect to each other to deposit said different kinds of molecular species at different locations on said substrate so that different locations are associated with said different kinds of molecular species.

30. The method of claim 29, further comprising applying a first electric field to said scanning probe microscope tip and said substrate so that said different kinds of molecular species move along said scanning probe microscope tip at different speeds towards said substrate.

31. The method of claim 30, wherein said different kinds of molecular species have different charge-to-mass ratios.

32. The method of claim 29, further comprising applying a second electric field, of opposite polarity to said first electric field, to said scanning probe microscope tip and said substrate to position said different kinds of molecular species toward a base of said scanning probe microscope tip, prior to moving said different kinds of molecular species towards said substrate for the purpose of separating said different kinds of molecular species.

33. The method of claim 30, wherein said first electric field is applied between said substrate and the base of said scanning probe microscope tip.

34. The method of claim 29, wherein the different locations are separated by at least 10 nanometers.

35. The method of claim 29, wherein the different locations are separated by at most 1 micrometer.

36. The method of claim 29, wherein the different locations are separated by at most 1 centimeter.

37. The method of claim 30, wherein labels, including at least one of proteins and fluorescent tags, are attached to at least some of said different kinds of molecular species to change at least one of charge and mass of said at least some of said different kinds of molecular species.

38. The method of claim 30, wherein the method is applied to separate different DNA fragments into respective groups on said substrate.

39. The method of claim 38, wherein said different DNA fragments are deposited at different locations.

40. The method of claim 30, wherein said scanning probe microscope tip is exposed to a solution, so that a coefficient of friction of said scanning probe microscope tip is altered, thereby promoting improved separation of said different kinds of molecular species.

* * * * *

UNITED STATES PATENT AND TRADEMARK OFFICE
CERTIFICATE OF CORRECTION

PATENT NO.       : 7,579,149 B2                                           Page 1 of 1
APPLICATION NO. : 11/047250
DATED            : August 25, 2009
INVENTOR(S)      : Frommer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 577 days.

Signed and Sealed this

Fourteenth Day of September, 2010

David J. Kappos
*Director of the United States Patent and Trademark Office*